US007060488B2

(12) United States Patent
Duong et al.

(10) Patent No.: US 7,060,488 B2
(45) Date of Patent: Jun. 13, 2006

(54) STACKED ARRAY OF REACTION RECEPTACLES

(75) Inventors: Vinh Duong, Hamburg (DE); Andreas Graff, Hamburg (DE); Cordula Kroll, Hamburg (DE); Werner Lurz, Kaltenkirchen (DE); Melanie Persson, Lauenburg (DE); Andreas Schirr, Bad Oldesloe (DE); Wilhelm Pluster, Boulder, CO (US); Lutz Timmann, Fuhlendorf (DE)

(73) Assignee: Eppendorf AG, Hamburg (DE)

( * ) Notice: Subject to any disclaimer, the term of this patent is extended or adjusted under 35 U.S.C. 154(b) by 723 days.

(21) Appl. No.: 10/352,526

(22) Filed: Jan. 28, 2003

(65) Prior Publication Data

US 2003/0148504 A1 Aug. 7, 2003

(30) Foreign Application Priority Data

Jan. 28, 2002 (DE) ................................ 102 03 441
Jan. 28, 2002 (DE) ................................ 102 03 456

(51) Int. Cl.
*C12M 1/34* (2006.01)

(52) U.S. Cl. .............................. 435/287.2; 435/288.5; 435/288.7; 422/102

(58) Field of Classification Search ..................... None
See application file for complete search history.

(56) References Cited

U.S. PATENT DOCUMENTS

| | | | |
|---|---|---|---|
| 4,902,624 | A | 2/1990 | Columbus et al. |
| 5,422,271 | A | 6/1995 | Chen et al. |
| 5,591,403 | A | 1/1997 | Gavin et al. |
| 5,764,356 | A | 6/1998 | Iwase et al. |

FOREIGN PATENT DOCUMENTS

| | | | |
|---|---|---|---|
| DE | 37 390 46 | A1 | 5/1988 |
| DE | 296 21 933 | U1 | 3/1997 |
| DE | 100 01 116 | A1 | 7/2001 |
| EP | 0 318 255 | A2 | 5/1989 |
| EP | 0 318 256 | A2 | 5/1989 |
| EP | 0 381 501 | A2 | 8/1990 |
| EP | 0 770 871 | A2 | 5/1997 |
| EP | 1 101 532 | A2 | 5/2001 |
| GB | 2 350 189 | A | 11/2000 |

OTHER PUBLICATIONS

WO 93/22058, Polynucleotide Amplification Analysis Using a Microfabricated Device, Publication No.: Nov. 11, 1993.

(Continued)

*Primary Examiner*—David A. Redding
(74) *Attorney, Agent, or Firm*—Rankin, Hill, Porter & Clark LLP

(57) ABSTRACT

A configuration of mini-volume reaction receptacles (1, 16, 41) of which the receptacle housings (2, 17) each enclose an elongated chamber (3, 18, 42) of which the ends are connected to apertures (6, 7, 20, 22) formed in the receptacle housing. The receptacle housings have identical base surfaces and have a small height relative to the base surface, and are stacked on one another while their base surfaces are mutually aligned. At least one aperture of a receptacle housing communicates with at least one aperture of a vertically adjacent receptacle housing, as seen in the direction of stacking. The receptacles (1, 16, 41) are mechanically interlocked in a direction transverse to the direction of stacking and can be plugged one into another. Each receptacle housing defines at least one aperture (6, 7, 22) at its top side that is accessible to a pipette.

12 Claims, 4 Drawing Sheets

OTHER PUBLICATIONS

WO 93/22055, Fluid Handling in Microfabricated Analytical Devices, Publication Date: Nov. 11, 1993.
WO 01/23093, Reaction System for Performing in the Amplication of Nucleic Acids, Publication Date: Apr. 5, 2001.
WO 01/77640 A2, Methods and Devices for Storing and Dispensing Liquids, Publication Date: Oct. 18, 2001.
WO 96/41864, Diode Laser Heated Micro-Reaction Chamber with Sample Detection Means, Publication Date: Dec. 27, 1996.
WO 97/10056, Device and Method for DNA Amplification and Assay, Publication Date: Mar. 20, 1997.
WO 96/14934, Mesoscale Sample Preparation Device and Systems for Determination and Processing of Analytes, Publication Date: May 23, 1996.

STACKED ARRAY OF REACTION RECEPTACLES

BACKGROUND OF THE INVENTION

1. Field of the Invention

The present invention relates to a configuration of mini-volume reaction receptacles of which the housings of each receptacle encloses an elongated chamber that, by its ends, is connected to apertures of the particular housing, and wherein the housings each have the same base surface and are of slight height relative to the base surface and are stacked one above the other while the base surfaces are mutually aligned, and wherein at least one aperture of one receptacle communicates with at least one aperture of a consecutive receptacle as seen in the order of stacking.

2. Description of the Related Art

A configuration of this kind is known from FIG. 6B of WO 96/14934. In this configuration, two receptacles are stacked one on the other within the cavity of a basic housing while subtending a communication passage. The chambers are designed for different purposes of reaction and allow carrying out different reactions on a specimen that, in sequence, is moved first into one of the chambers and then is moved through the communication passage into the other chamber. Such a design allows a number of different applications. For instance, one chamber may be used to purify DNA material and PCR (polymerase chain reaction) may be carried out in the next chamber. As indicated in FIG. 7 of the document, the design may be modified by being fitted with a heater for the PCR chamber.

The known basic design of this housing comprising the stacked array is required to support in place the stack and includes intake and outlet ducts to supply specimen material to the chambers. However, the basic housing also demands substantially large areas exceeding by far the base area of the chamber cases. Moreover, the required basic housing entails substantial increases in costs.

A stacked array of two chambers is known from U.S. Pat. No. 4,902,624, wherein the chambers are received compactly in one common housing. This design allows an array of several tightly adjacent receptacles that may be serviced jointly through the pipette tips of a multiple pipette configured in the conventional grid of a micro-titration tray. The chamber configuration of the US '624 patent is fitted for such purposes with a pipette-accessible aperture at its top.

However, the application of the US '624 patent incurs the drawback of the firmly integrated configuration of the two chambers, thereby constraining use of the two chambers only in a fixed relation. Using the chambers individually or changing, for instance, the sequence of the chambers or the number of chambers required in a given process is precluded.

SUMMARY OF THE INVENTION

The present invention is directed toward a stacked array of the above kind wherein the individual chambers are exchangeable and may be stacked one on the other in the desired sequence while nevertheless making it possible to operate with a compact, stacked array in applications using a multi-pipette.

In the invention, the particular chambers of identical base area that is on the same array of base areas may be superposed on each other into arbitrary heights. The mutual geometric interlock assures fixing the stack in place and, accordingly, a basic housing requiring additional area is not needed. The stack's housings subtend between themselves chamber communications and, as a result, specimens may be sequentially pumped through various chambers for the purpose of implementing consecutive reactions. Each housing is fitted at its top side with an aperture for pipette access, pipetting may be carried out at arbitrary stack heights into the particular uppermost housing. The housings being relatively dismantlable, the individual housings also may be used for individual reactions independently of other housings, or they may serve as preliminary reaction stages in order to allow subsequent further reactions in other chambers. The pipette which shall be set on the uppermost housing may be used to pump specimen liquid through the chambers, wherein the pipette communicating with that chamber that at the time contains a reaction specimen. Accordingly, a small array area with conventional multi-pipette configurations suffices to set up a serviceable stack that may be applied in a highly versatile manner by exchanging or interchanging chambers to the most diverse reactions even including a very large number of reaction stages.

The geometric interlock between the chamber housings may be implemented by special clamps or plug-in devices. Preferably, however, the interlinked apertures themselves act also as plug-in devices, as a result of which housing manufacture shall be substantially simplified and far more economical.

In further accordance with the present invention, the pipette-accessible apertures in the form of recesses together with corresponding protrusions of the above housing may create the plug-in connection, again simplifying manufacture.

As already mentioned above, the housings may receive different chambers for different purposes. One or more chambers may be fitted for PCR purposes. This entails regulated chamber heating which, as in the initial, first-cited documents, may be in the form of a small heating element situated near the chamber. Advantageously, however, if the lowermost reaction receptacle of the stack is used for PCR functions, then it may be conventionally placed on the top surface of a PCR cycler block and be temperature-regulated at its bottom surface, thereby attaining highly effective temperature regulation.

The present invention offers the advantage of a better wall/volume ratio, and this improved wall/volume ratio is advantageous with respect to PCR and also to chambers with wall-bound reagents and furthermore for other purposes. In addition this design of the invention offers the advantage of improved rinsing in the absence of dead corners.

The present invention further offers the advantage of simple manufacture particularly applicable to PCR chambers in order to attain a planar surface allowing good temperature regulation and being thermally highly conductive, for instance by making the tray out of metal. The present invention further provides improved rapid temperature regulation of the entire chamber volume.

In further accordance with the present invention, a chamber is in the form of a narrow duct. On account of the capillarity of the narrow, elongated chamber, the specimen shall be well cohesive, that is it will not tear apart during pumping. Moreover, mixing a specimen may be improved by repeated pumping in both directions.

Further, if the filling aperture is made narrower and, in particular, is made capillary, good suction on the filling aperture will be assured and allows residue-free emptying by suction at the filling aperture.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
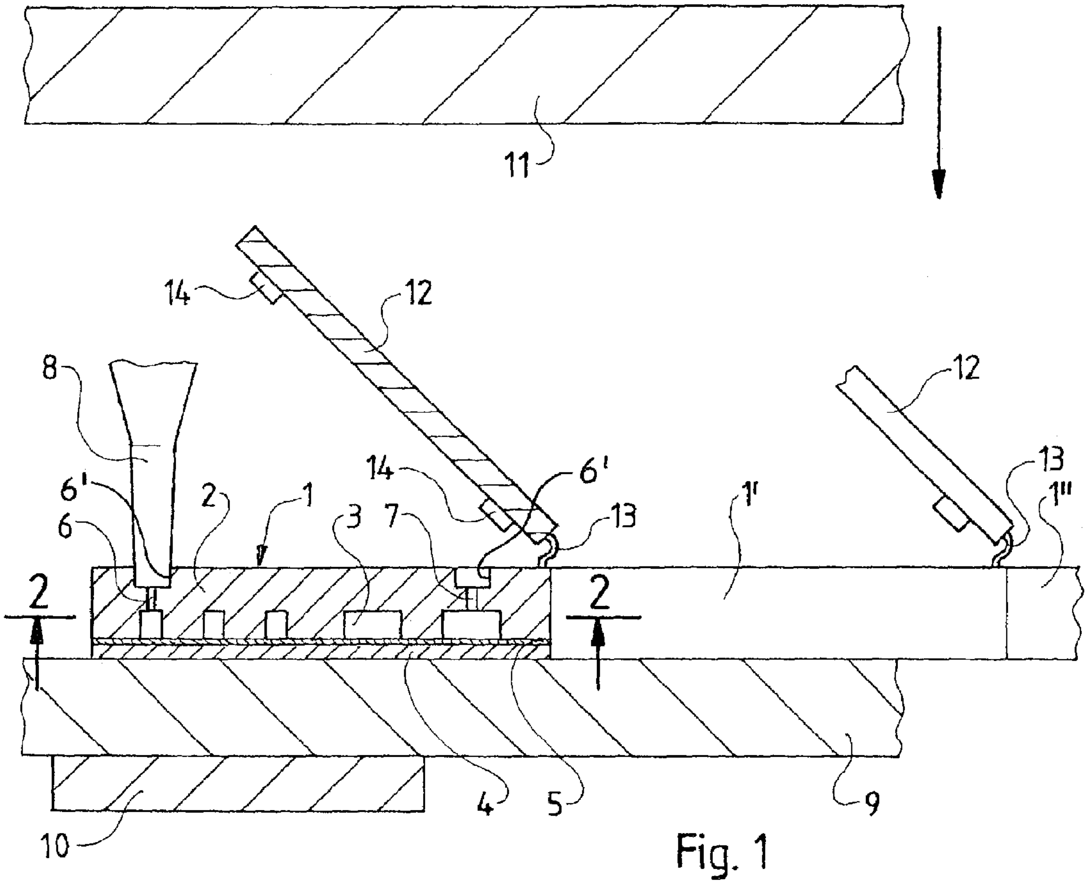
FIG. 1 is a longitudinal section along line 1—1 of the reaction receptacle shown in FIG. 2 mounted on the temperature-regulating block of a thermo-cycler.
Figure 2:
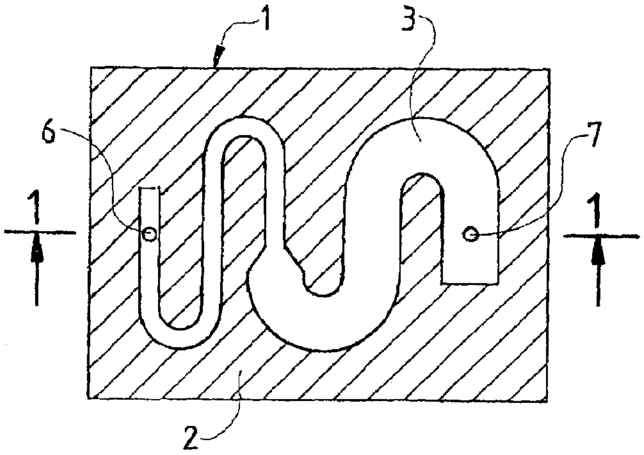
FIG. 2 is a section along line 2—2 in the FIG. 1.

FIGS. 1 and 2 show a reaction receptacle 1 comprising a rectangular housing 2 made of an appropriate plastic. A reaction chamber 3 is formed into the underside of the housing 2 in the form of a recess and is covered downward by a metal foil 4, which is coated with a plastic layer 5 on the side facing the housing 2. By means of the plastic foil 5, the metal foil 4 may be bonded to the lower surface of the housing 2 or be joined to it thermally, for instance by hot-sealing. In this manner, the reaction chamber 3 is closed on all sides.

The reaction chamber 3 is in the form of an elongated duct running in a winding or serpentine manner around several bends. At its ends, the duct is open by means of apertures 6, 7 with respect to the top side of the housing 2. As shown by FIG. 1, each of the apertures 6, 7 is fitted at its upper free end with a recess 6' that, illustratively, may sealingly receive a pipette tip 8. The reaction chamber 3 may be filled from the pipette tip through the aperture 6, with the other aperture 7 being used for ventilation.

The reaction receptacle shown in FIG. 1 is used for PCR. Using the pipette tip 8 shown in FIG. 1, first a specimen containing a nucleic acid to be amplified may be fed into the reaction chamber 3. Using the same or another pipette tip 8, the mixture of reagents required for PCR may then be added. Thereupon, thorough mixing of the inserted mixture may be attained by advancing and retracting the mixture in the elongated duct constituted by the reaction chamber 3. This process is enhanced by the narrow cross-section of the chamber 3 and, furthermore, by turbulence and shearing forces generated at the chamber's bends. As shown by FIG. 2, the cross-section of the chamber widens at its end that is toward the aperture 7. This feature also increases mixing.

As shown in FIG. 2, the chamber 3 is very elongated and exhibits a tiny cross-section that preferably exerts, at least in the vicinity of the intake aperture 6, a capillary effect on the liquid. As a result, capillarity will keep the liquid together and this liquid remains stressed in the vicinity of the intake aperture, as a result of which it may not only be introduced through the aperture 6 but also be aspirated again by it without residues remaining in the chamber 3. In this manner, problem-free filling, to-and-fro motion (for the purpose of mixing), and withdrawal through the aperture 6 is feasible.

Moreover, the narrow geometry of the chamber 3 assures that even in the presence of small quantities of introduced liquid, there shall be filling of a segment wherein the liquid coheres in a bubble-free manner and exhibits surfaces only at the front and rear ends of the liquid-filled segment. These surfaces are small and the interfering evaporation arising during raised PCR temperatures is substantially averted.

It must be borne in mind that the entire reaction chamber is planar and situated at a very small distance from the metal foil 4. As a result, it may be temperature-regulated by the foil.

The metal foil 4 may be heated and cooled in different ways in order to temperature-regulate the specimen in the reaction chamber 3. Applicable heating may illustratively be direct heating of the metal foil 4 by passing an electric current through it. Furthermore, the shown reaction receptacle 1 also may be directly set on the surface of a Pettier element in order to be selectively heated or cooled by the Pettier element.

However, FIG. 1 shows that the reaction receptacle 1, together with the metal foil 4 constituting the temperature-regulating surface of the reaction receptacle 1, is mounted on the surface of a temperature-regulation block 9 of a substantially commercial thermo-cycler. As regards the present purposes, the temperature-regulating block 9 may be a simple flat plate that is very thin and therefore of little heat capacity, whereby the block may act quickly in its temperature regulation. Illustratively, Peltier elements are mounted underneath the temperature-regulating block 9, of which one element is shown as 10 in FIG. 1.

The shown planar design of the reaction receptacle 1 is suitable for configuration in juxtaposition with further identical reaction receptacles 1' and 1" on the temperature-regulating block 9. A lid 11 may be lowered onto the reaction receptacles and force them against the temperature-regulating block 9 to attain improved heat transfer.

FIG. 1 also shows that the reaction receptacle 1 may be fitted with a sealing cap 12, which is secured by a strap 13 to the housing 2 of the reaction receptacle 1. The sealing cap 12 is fitted with sealing protrusions 14, which in a sealing manner may engage the particular recess at the upper end of the apertures 6, 7 of the chamber 3 in order to seal the chamber. In the closed position the lid 11 may press against the flat top side of the sealing cap 12.

In a variation of the above described embodiment, the chamber 3 also may assume other geometries, for instance being a round or rectangular planar chamber, care being required that all volume elements of the chamber always must be near the temperature-regulating metal foil 4. In a variation of the above-discussed embodiment, the metal foil 4 may be eliminated and only a plastic foil 5 may be used which, when very thin, will also offer excellent heat transfer.

Figure 3:
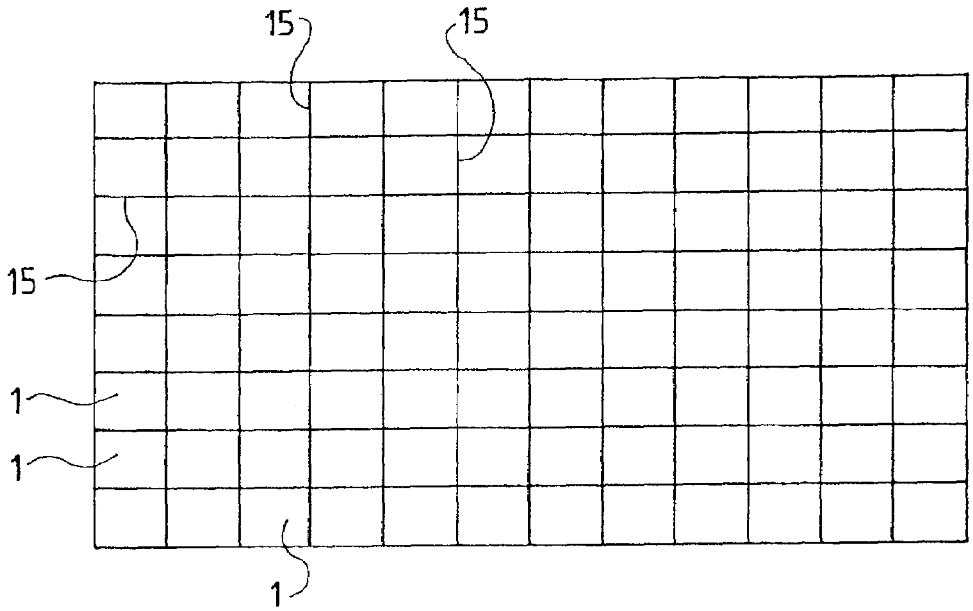
FIG. 3 is a planar block constituted by several reaction receptacles.

On a smaller scale, FIG. 3 shows a topview of the assembly of FIG. 1 and that a substantial number of the rectangular reaction receptacles 1 may be juxtaposed in rows and columns, for instance in the conventional 8×12 configuration of a total of 96 receptacles. As shown by FIG. 1, these receptacles may be mutually abutting. Such abutting configuration may be assured, for instance, by geometrically interlocking the reaction receptacles. For that purpose they may be fitted at their abutting sides with appropriate protrusions. These receptacles, moreover, are designed to allow stacking them.

Figure 4:
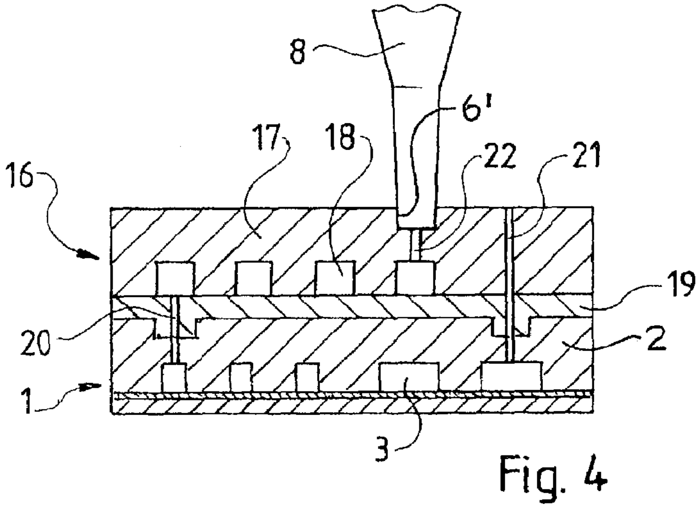
FIG. 4 is a receptacle—used for purifying nucleic acid—in the stacked position on the reaction receptacle of FIG. 1.

FIG. 4 shows the reaction receptacle 1 of FIGS. 1 and 2 in the stacked configuration with a superposed purification receptacle 16, which is very similar to the reaction receptacle 1. The receptacle 16 comprises a plastic housing 17 wherein, just as in the reaction receptacle 1, a purification chamber 18 is subtended at the underside and initially is open. The purification chamber 18 is closed by a plate 10 which, in this instance, need not be a thin foil and which is connected in an appropriate manner to the housing 17 so as to seal it. A purification chamber 18 is subtended in the embodiment in the form of an elongated duct and cross-sectionally resembles the reaction chamber 3 of FIG. 2.

The plate 19 comprises two downward pointing adapters each fitting into the recess 6' of the apertures 6 and 7 of the reaction receptacle 1. A duct 20 connected to the purification chamber 18 also communicates with the filling aperture 6 of the reaction chamber 3 and a duct 21, acting as the venting duct and passing through the housing 17 of the purification receptacle 16 freely upward for ventilation, communicates with the other aperture 7 of the reaction chamber 3. The other end of the purification chamber 18 not connected to the duct 20 communicates with a duct 22 running to the top side of the housing 17 and comprising at its top side a recess 6' to receive the pipette tip 8.

Figure 5:
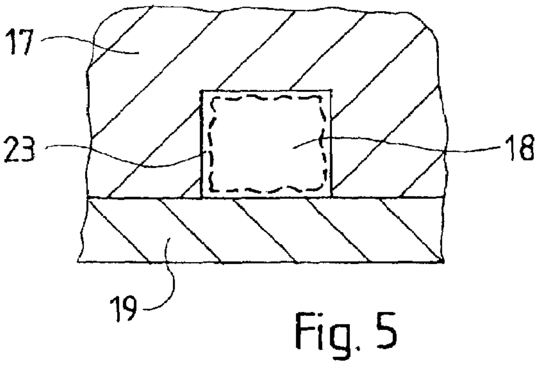
FIG. 5 is an enlarged detail of the duct of the purifying receptacle of FIG. 4.

The purification chamber 18 is used to purify the nucleic acid present in a specimen to be tested before PCR is carried out. As shown by FIG. 5, the wall of the purification chamber 18 is fitted for that purpose with an appropriate layer 23, which is bonded to the wall and which exhibits properties to retain nucleic acid under given, selected circumstances, and to release the nucleic acid under other given, selected circumstances.

The full procedure carried out in the configuration of FIG. 4 may be controlled by the pipette tip 8. First, the pipette tip feeds the specimen containing the nucleic acids into the purification chamber 18. Then, the nucleic acids are immobilized in the purification chamber 18 at the layer 23. Accordingly, the chamber 18 may be purified by introducing and evacuating liquid. Thereupon, and under appropriate conditions, liquid may be supplied to absorb the newly released nucleic acids and transfer them through the duct 20 into the reaction chamber 3 of the reaction receptacle 1. The reagents implementing PCR may already have been admixed or be post-fed in a second stage from the pipette tip 8. Thereupon, the reaction chamber 3 is heated and cooled through the foil 4 and PCR is carried out. Next, the product enriched by amplification nucleic acid may be evacuated.

In a variant regarding the housings 2 and 17 shown in FIG. 4, such housings also may be constituted, for instance, by two mutually merging chambers. The housings 2 and 17 retain the same planar geometry and base surfaces as shown in FIG. 4 in order that they may be stacked with other housings, for instance receiving only one chamber.

After being taken apart, the two housings 2 and 17 of FIG. 4 may also be used alone, in particular the housing 2 receiving the PCR chamber 3.

Illustratively, the shown receptacles 1 and 16 may be externally rectangular as shown above at a base surface (FIG. 2) with edge lengths of roughly 10 mm and a height (FIG. 1) perpendicularly to the surface of the temperature-regulating block 9 roughly of 1 mm (or a few mm). The total volume of the chambers 3 or 18 may be roughly 20 μltr, whereby specimens of a few μltr may be used.

A stacked configuration of these housings may be configured in the array of FIG. 3 on an array surface and, as a result, stacked configurations may be juxtaposed in the array. The array of FIG. 3 then may be serviced simultaneously by pipette tips 8 also configured in a matching array.

Figure 6:
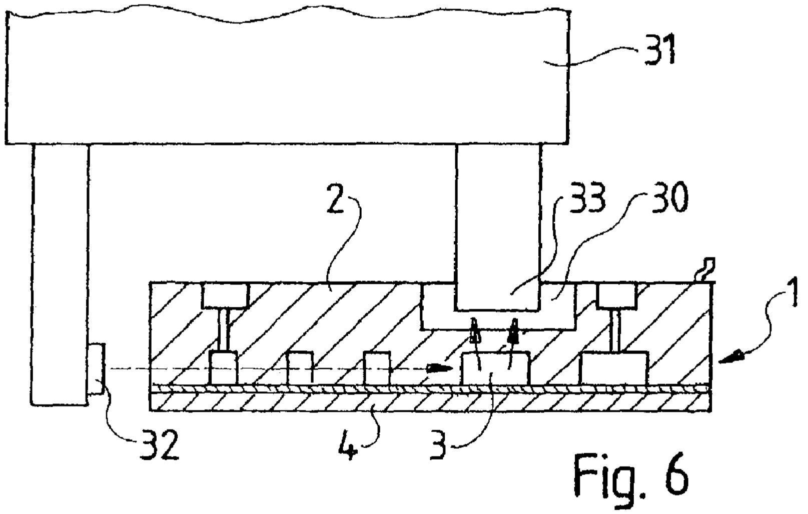
FIG. 6 is a section corresponding to FIG. 1 of the reaction receptacle shown in a variation for optical investigations.
Figure 7:
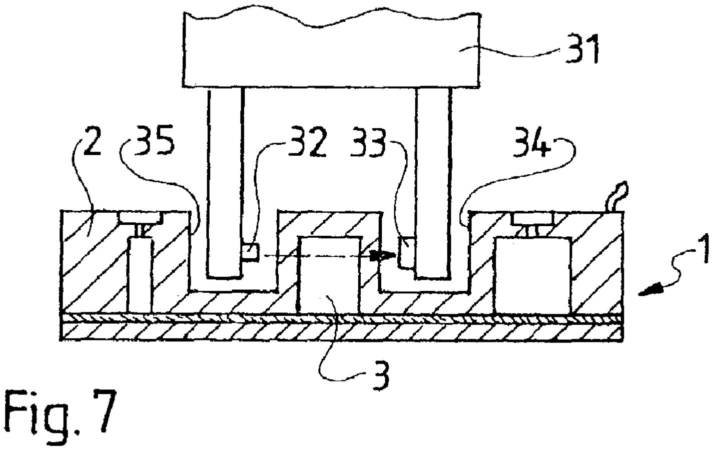
FIG. 7 shows a further variation in the manner of FIG. 6.
Figure 8:
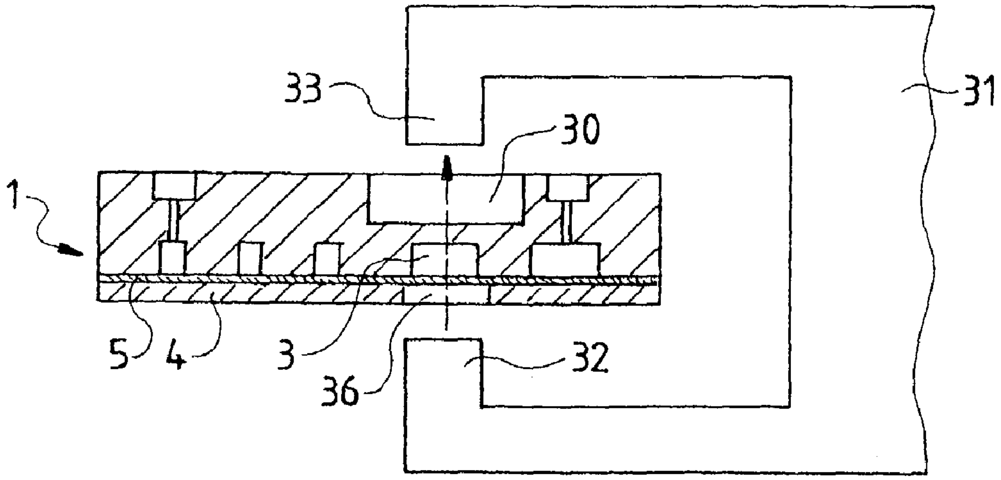
FIG. 8 shows a further variation corresponding to that of FIG. 6.

FIGS. 6 through 8 show variations of the reaction receptacle 1, the reference numerals used heretofore being retained as much as possible.

The reaction receptacle 1 of FIG. 6 corresponds to that of FIG. 1 except for a recess 30 above one of the segments of the chamber 3. As a result, only a very thin wall of the housing 2 exists above the chamber 3 in the zone of the recess 30. The entire housing 2 is made of an optically transparent material.

A detection device 31 is shown mounted in such a manner to the reaction receptacle 1 that, by means of an optical transmitter 32, it irradiates the housing 2 laterally as far as the chamber zone underneath the recess 30. An optical receiver 33 enters the recess 30 to test fluorescent light in the chamber 3.

The reaction receptacle 1 may rest on the temperature-regulating block 9 of FIG. 1 and PCR may be carried out in it. The detection device 31 may monitor, by means of appropriate procedures, amplification taking place during PCR.

As regards the embodiment of FIG. 6, the optical path denoted by the arrows runs at an angle through the housing. This configuration is therefore suitable for fluorescence.

FIGS. 7 and 8 show variations operating on the basis of a straight optical path and therefore being appropriate not only for fluorescence but also for photometric processes.

As regards the embodiment of FIG. 7, the housing 2 is fitted at its top side with two recesses 34, 35 situated one on each side of a segment of the chamber 3. The transmitter 32 and the receiver 33 of the detector device 31 dip into the two recesses 34, 35, and, in this embodiment, the transmitter and the receiver point at each other. Accordingly, in this embodiment mode, a zone of the chamber may be irradiated along a straight path and, consequently, optical measurements may be taken in order to monitor reactions in the chamber 3 or to investigate reaction products.

FIG. 8 shows a variation of the embodiment of FIG. 7. In this instance, the design of the reaction receptacle 1 substantially corresponds to that of FIG. 6. However, a window 36 has been cut out of the metal foil 4 underneath the recess 30. In the zone of the window, the chamber 3 is only sealed off by the plastic coating 5. In this embodiment, the transmitter 32 and the receiver 33 of the detection device 31 are configured underneath and also above the reaction receptacle 1 as shown in FIG. 8. This embodiment is inappropriate for PCR. However, the reaction receptacle 1 according to this embodiment may be used as a cuvette.

As regards the embodiments of FIGS. 6 through 8, and provided the design is appropriate, the purification receptacle 16 also may be used instead of the reaction receptacle in order to monitor the progress of purification in the receptacle 16 or to merely use it as a cuvette for appropriate detection purposes.

Figure 9:
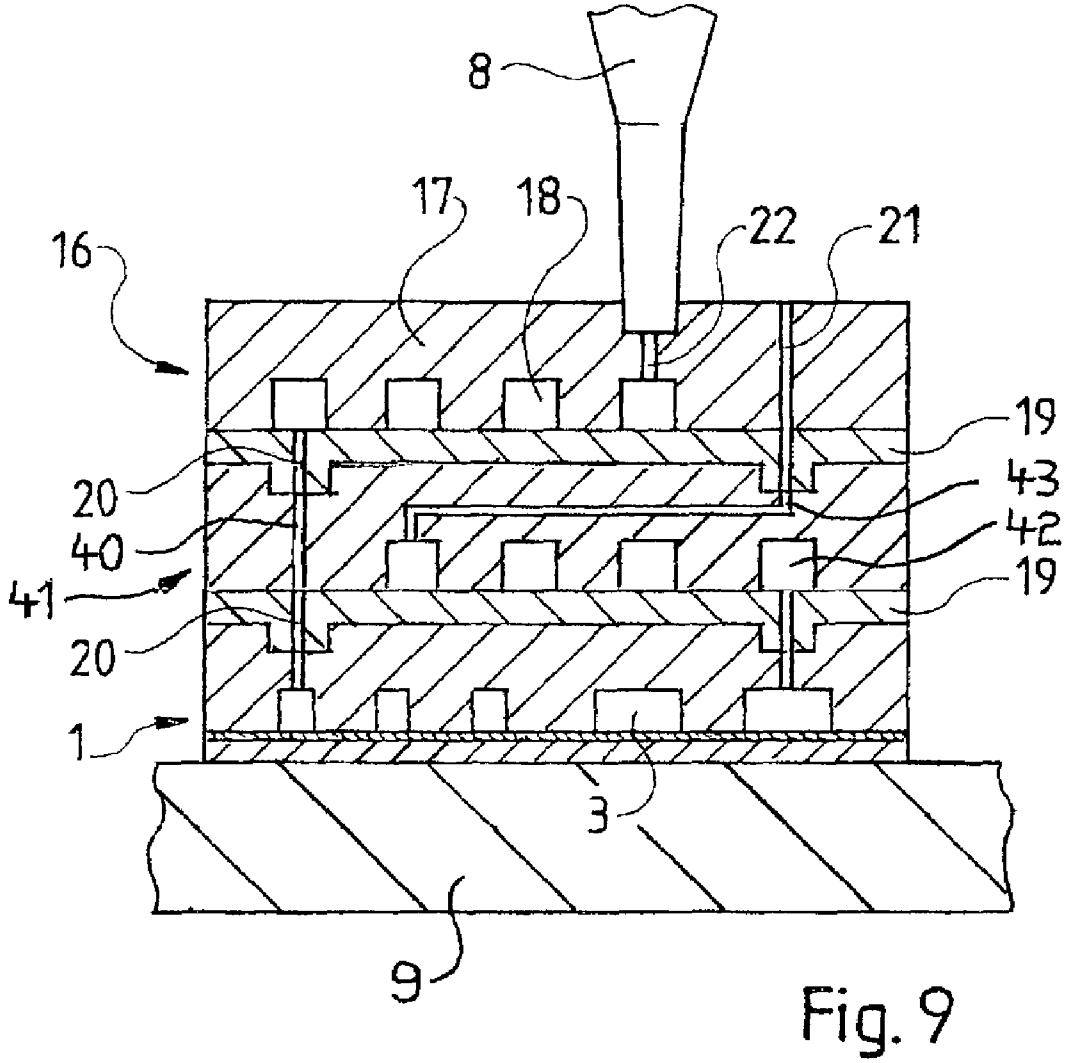
FIG. 9 shows a stack of FIG. 4 but with three mutually stacked reaction receptacles.

FIG. 9 shows a stack configuration corresponding to that of FIG. 4, but in this instance comprising three superposed reaction receptacles. The reaction receptacle 1 situated at the bottom of the stack corresponds to that shown in FIG. 1 or to the lower receptacle shown in FIG. 4 and is used for PCR. It rests on the temperature-regulating block 9 of FIG. 1.

The uppermost reaction receptacle 16 corresponds to the receptacle of FIG. 4 and is used for DNA purification before implementing PCR. It is fed from the pipette 8 which, after purification, presses the specimen through a transfer duct 40 of the center reaction receptacle 41 toward the PCR chamber 3 of the lowermost receptacle 1. After the execution of the PCR in chamber 3 of the lowermost receptacle 1; the pipette forces the specimen upward into the chamber 42 of the center reaction receptacle 41, the chamber 42 being, for example, embodied as shown in topview in FIG. 2. After the specimen has passed through this chamber and after carrying out a scheduled reaction therein, the specimen may be withdrawn again consecutively through all chambers by means of the pipette 8. At its free end, the chamber 42 communicates through a duct 43 with the venting duct 21 of the uppermost reaction receptacle 16 in order to allow venting during the to-and-fro motion of the specimen in the chambers of the stack configuration, that is, to preclude any backing up.

Again the stack configuration of FIG. 9 may be designed to match the array of FIG. 3 in order that a matching multi-pipette may jointly service several stacks juxtaposed in an array.

As regards special applications, and by increasing the stacking height, further reaction receptacles fitted with special chambers appropriately communicating with each other may be constituted in order to carry out a series of consecutive reactions.

The invention claimed is:

1. A configuration of mini-volume reaction receptacles (1, 16, 64) comprising a plurality of receptacle housings (2, 17), each receptacle housing defining an elongated chamber (3, 18, 42), each elongated chamber having a first end fluidly connected to an aperture (6, 7, 20, 22) formed in the receptacle housing and a second end fluidly connected to another aperture formed in the receptacle housing, where each receptacle housing has a base surface and a height, said height being small as compared to the base surface, and wherein the receptacle housings are stacked one above the other such that the base surfaces of said receptacle housings are in mutual alignment, at least one aperture of one receptacle housing being in fluid communication with at least one aperture of a vertically adjacent receptacle housing, and wherein adjacent receptacles (1, 16, 41) cooperate to provide a mutual mechanical interlock in a direction transverse to stacking and are designed to be superposed on one another, and wherein each receptacle comprises at least one further aperture (6, 7, 22) at its top side to allow access to a pipette.

2. The configuration as claimed in claim 1, wherein the superposed receptacles include an upper receptacle and a lower receptacle and wherein said at least one apertures of said upper and lower receptacles cooperate to define plug-in connectors.

3. The configuration as claimed in claim 2, wherein the at least one further aperture (6) of the lower receptacle includes a recess (6') to receive a pipette (8), and wherein the at least one aperture (20) of the upper receptacle is fitted with a protrusion engaging the at least one further recess of the lower receptacle in a mechanically interlocking manner.

4. The configuration as claimed in claim 1, wherein a lowermost receptacle (1) is a PCR reaction receptacle.

5. The configuration as claimed in claim 1, wherein at least one of the elongated chambers is a narrow duct (18).

6. The configuration as claimed in claim 1, wherein the elongated chamber (3, 18) of at least one receptacle (1, 16) is a recess in the receptacle housing (2, 17) and wherein the recess is sealingly covered by a plate (4, 19) that is bonded to the receptacle housing (2, 17).

7. The configuration as claimed in claim 4, wherein the elongated chamber (3) is a planar chamber that is arranged such that a volume of said planar chamber is close to and parallel with a flat bottom surface (4) of the receptacle housing.

8. The configuration as claimed in claim 5, wherein a cross-section of the elongated chamber (3, 18, 42) is selected so as to provide capillary flow along at least portions of a length of the elongated chamber.

9. The configuration as claimed in claim 5, wherein the elongated chamber (3, 18, 42) extends in a path between said ends, and wherein said path includes one or more bends.

10. The configuration as claimed in claim 5, wherein the chamber (3, 18, 42) has varying cross-sectional dimensions along its length.

11. The configuration as claimed in claim 10, wherein the cross-section of the chamber (3, 18, 42) narrows toward the at least one further aperture (6).

12. The configuration as claimed in claim 1, wherein at least one receptacle comprises a chamber (18) having an inside wall whose surface area is large as compared to a volume of said chamber, said inside wall comprising a layer (23) to purify nucleic acid being detachably affixed to said inside wall.

* * * * *